United States Patent
Wang et al.

(10) Patent No.: US 6,552,162 B1
(45) Date of Patent: Apr. 22, 2003

(54) WATER-RESPONSIVE, BIODEGRADABLE COMPOSITIONS AND FILMS AND ARTICLES COMPRISING A BLEND OF POLYLACTIDE AND POLYVINYL ALCOHOL AND METHODS FOR MAKING THE SAME

(75) Inventors: James H. Wang, Appleton, WI (US); David M. Schertz, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/525,547

(22) Filed: Mar. 14, 2000

Related U.S. Application Data (63) Continuation-in-part of application No. 08/903,866, filed on Jul. 31, 1997, now Pat. No. 6,075,118.

(51) Int. Cl.[7] .............................................. C08G 63/08
(52) U.S. Cl. .................. 528/354; 528/355; 528/361; 525/63; 525/67; 525/162
(58) Field of Search ................................ 528/354, 355, 528/361; 525/63, 67, 162

(56) References Cited

U.S. PATENT DOCUMENTS

| | | |
|---|---|---|
| 3,806,495 A | 4/1974 | Schoen |
| 4,284,671 A | 8/1981 | Cancio et al. |
| 4,504,635 A | 3/1985 | Weber, Jr. et al. |
| 4,526,938 A | 7/1985 | Churchill et al. |
| 4,620,999 A | 11/1986 | Holmes |
| 4,683,287 A | 7/1987 | Koleske et al. |
| 4,701,483 A | 10/1987 | Okitsu |
| 4,745,160 A | 5/1988 | Churchill et al. |
| 4,767,829 A | 8/1988 | Kordemenos et al. |
| 4,826,493 A | 5/1989 | Martini et al. |
| 4,826,945 A | 5/1989 | Cohn et al. |
| 4,933,182 A | 6/1990 | Higashi et al. |
| 5,136,017 A | 8/1992 | Kharas et al. |
| 5,278,202 A | 1/1994 | Dunn et al. |
| 5,300,576 A | 4/1994 | Nemphos et al. |
| 5,322,925 A | 6/1994 | Muth et al. |

(List continued on next page.)

FOREIGN PATENT DOCUMENTS

| | | |
|---|---|---|
| EP | 241178 | 10/1987 |
| EP | 0654504 | 4/1995 |
| EP | 0704470 | 3/1996 |
| JP | 6-142127 | 5/1994 |
| JP | 6-298921 | 10/1994 |
| JP | 8-239457 | 9/1996 |
| WO | 92/04412 | 3/1992 |
| WO | WO 94/07941 A1 | 4/1994 |
| WO | 94/10257 | 5/1994 |
| WO | WO 98/29506 A1 | 7/1998 |
| WO | WO 99/06456 A1 | 2/1999 |

OTHER PUBLICATIONS

Williams et al. Biodegradable Plastics from Plants *Chemtech* 38–44 1996.

Ikejima, T., et al. Infrared Analysis on Blends of Poly (3–Hydrooxybutyric Acid) and Stereoregular Poly (Vinyl Alcohol): Influence of Tecticity of Poly (Vinyl Alcohol) on Crystallization of Poly (3–Hydroxybutyric Acid) *Macromolecular Chemistry and Physics* 197(3 869–880 1996).

*Primary Examiner*—Duc Truong
(74) *Attorney, Agent, or Firm*—Kilpatrick Stockton LLP (57) ABSTRACT

The present invention is a water-responsive blend of a polylactide and a polyvinyl alcohol. The present invention includes films and personal care articles comprising a blend of a polyvinyl alcohol and a polylactide and includes a method of making such films and articles and a method of varying the water responsiveness of such films and articles. In a preferred embodiment, the compositions, films and articles comprise a blend of polyvinyl alcohol and modified polylactide. The compositions and films described herein are useful as a component in flushable and degradable articles.

22 Claims, 3 Drawing Sheets

U.S. PATENT DOCUMENTS

| | | |
|---|---|---|
| 5,342,659 A | 8/1994 | Horowitz et al. |
| 5,360,892 A | 11/1994 | Bonsignore et al. |
| 5,410,016 A | 4/1995 | Hubbell et al. |
| 5,417,983 A | 5/1995 | Nagase et al. |
| 5,422,387 A | 6/1995 | Toms et al. |
| 5,434,241 A | 7/1995 | Kim et al. |
| 5,470,944 A | 11/1995 | Bonsignore |
| 5,508,101 A | 4/1996 | Patnode et al. |
| 5,525,671 A | 6/1996 | Ebato et al. |
| 5,567,435 A | 10/1996 | Hubbell et al. |
| 5,567,510 A | 10/1996 | Patnode et al. |
| 5,574,129 A | 11/1996 | Miyoshi et al. |
| 5,583,187 A | 12/1996 | Sharak et al. |
| 5,612,052 A | 3/1997 | Shalaby |
| 5,658,977 A | 8/1997 | Yang et al. |

WATER-RESPONSIVE, BIODEGRADABLE COMPOSITIONS AND FILMS AND ARTICLES COMPRISING A BLEND OF POLYLACTIDE AND POLYVINYL ALCOHOL AND METHODS FOR MAKING THE SAME

CROSS-REFERENCE TO RELATED APPLICATIONS

The present application is a continuation-in-part of application Ser. No. 08/903,866 filed Jul. 31, 1997, now U.S. Pat. No. 6,075,118.

FIELD OF THE INVENTION

The present invention relates to water-responsive compositions and films, fibers and articles comprising such compositions. The present invention includes methods of making and varying the water-responsiveness of such compositions. The compositions of the present invention comprise a blend of poly(vinyl alcohol) and a polylactide. In one embodiment, the polylactide is grafted with a polar vinyl monomer.

BACKGROUND OF THE INVENTION

Even though the amount of plastics, more precisely polymers, used in a variety of consumer goods, packaging and medical articles has not significantly increased over the past twenty years, the common perception is that more and more non-degradable plastics are filling up our limited landfill space. Despite this perceived disadvantage, polymers continue to be used in the manufacture of consumer goods, packaging and medical articles because polymers offer many advantages over the more traditional materials: wood, glass, paper, and metal. The advantages of using polymers include decreased manufacturing time and costs, improved mechanical and chemical properties, and decreased weight and transportation costs. It is the improved chemical resistance properties of the majority of plastics that result in their non-degradability.

Disposal of waste materials, including food waste, packaging materials and medical waste, into a typical landfill provides a relatively stable environment in which none of these materials is seen to decompose at an appreciable rate. Alternative waste disposal options have been increasingly discussed and utilized to divert some fractions of waste from entombment in landfills. Examples of these alternatives include municipal solid waste composting, anaerobic digestion, enzymatic digestion, and waste water sewage treatment.

Much controversy is associated with the disposal of medical waste. Both government agencies and members of the private sector have been increasingly directing in-depth scrutiny and funds toward this subject. Admittedly, concerns over the fate of materials contaminated with infectious substances are valid and proper measures to insure the safety of health care workers and the general public should be taken.

Currently, medical waste can be categorized as either reusable or disposable. Categorization as to whether certain waste is reusable or disposable is customarily determined according to the material from which the article was constructed and the purpose for which the article was used.

After use, reusable medical articles are cleansed and sterilized under stringent conditions to ensure disinfection. In comparison, disposable medical articles are usually only used once. Even then, disposing procedures are not straightforward, rather they often involve several steps to safeguard against potential hazards. Typically, after use, disposable medical articles must be disinfected or sterilized, adding a significant cost prior to disposal into a specially designated landfill or waste incinerator. As a result, the disposal cost for the contaminated single use articles is quite high.

Despite the high cost of disposal, single use medical articles are desirable because of the assurance of clean, and uncontaminated equipment. Many times in the medical context, sterilization procedures conducted improperly can result in detrimental effects such as the transmission of infectious agents from one patient to another. Improper sterilization can also be disastrous in a laboratory setting, where, for example, contaminated equipment can ruin experiments resulting in tremendous costs of time and money.

Currently, disposable medical fabrics are generally composed of thermoplastic fibers of non-degradable materials such as polyethylene, polypropylene, polyesters, polyamides and acrylics. These fabrics can also include mixtures of thermoset fibers such as polyamides, polyarimides and cellulosics. They are typically 10–100 grams per square yard in weight and can be woven, knitted or otherwise formed by methods well known to those in the textile arts while the non-wovens can be thermobonded, hydroentangled, wet laid or needle punched and films can be formed by blow or cast extrusion or by solution casting. Once used, these fabrics are difficult and costly to dispose of and are non-degradable.

The use of polymers for various disposable articles is widespread and well known in the art. In fact, the heaviest use of polymers in the form of film and fibers occurs in the packaging and the disposable article industries. Films employed in the packaging industry include those used in food and non-food packaging, merchandise bags and trash bags. In the disposable article industry, the general uses of polymers occurs in the construction of diapers, personal hygiene articles, surgical drapes and hospital gowns, instrument pads, bandages, and protective covers for various articles.

In light of depleting landfill space and inadequate disposal sites, there is a need for polymers which are water-responsive. Currently, polymers such as polyethylene, polypropylene, polyethylene terephthalate, nylon, polystyrene, polyvinyl chloride and polyvinyldene chloride are popular for their superior extrusion and film and fiber making properties. However, these polymers are not water-responsive. Furthermore, these polymers are generally non-compostable, which is undesirable from an environmental perspective.

Polymers and polymer blends have been developed which are generally considered to be water-responsive. These are polymers which purportedly have adequate properties to permit them to breakdown when exposed to conditions which lead to composting. Examples of such arguably water-responsive polymers include those made from starch biopolymers and polyvinyl alcohol.

Although materials made from these polymers have been employed in film and fiber containing articles, many problems have been encountered with their use. Often the polymers and articles made from these polymers are not completely water-responsive or compostable. Furthermore, some water-responsive polymers may also be unduly sensitive to water, either limiting the use of the polymer or requiring some type of surface treatment to the polymer, often rendering the polymer non water-responsive. Other polymers are undesirable because they have inadequate heat resistance for wide spread use.

Personal care products, such as diapers, sanitary napkins, adult incontinence garments, and the like are generally constructed from a number of different components and materials. Such articles usually have some component, usually the backing layer, constructed of a liquid repellent or water-barrier polymer material. The water-barrier material commonly used includes polymer materials such as polyethylene film or copolymers of ethylene and other polar and nonpolar monomers. The purpose of the water-barrier layer is to minimize or prevent absorbed liquid that may, during use, exude from the absorbent component and soil the user or adjacent clothing. The water-barrier layer also has the advantage of allowing greater utilization of the absorbent capacity of the product.

Although such products are relatively inexpensive, sanitary and easy to use, disposal of a soiled product is not without its problems. Typically, the soiled products are disposed in a solid waste receptacle. This adds to solid waste disposal accumulation and costs and presents health risks to persons who may come in contact with the soiled product. An ideal disposal alternative would be to use municipal sewage treatment and private residential septic systems by flushing the soiled product in a toilet. Products suited for disposal in sewage systems are termed "flushable". While flushing such articles would be convenient, prior art materials do not disintegrate in water. This tends to plug toilets and sewer pipes, frequently necessitating a visit from a plumber. At the municipal sewage treatment plant, the liquid repellent material may disrupt operations by plugging screens and causing sewage disposal problems. It therefore is necessary, although undesirable, to separate the barrier film material from the absorbent article prior to flushing.

In addition to the article itself, typically the packaging in which the disposable article is distributed is also made from a water-barrier, specifically water-resistant, material. Water-resistivity is necessary to prevent the degradation of the packaging from environmental conditions and to protect the disposable articles therein. Although this packaging may be safely stored with other refuse for commercial disposal, and especially in the case of individual packaging of the products, it would be more convenient to dispose of the packaging in the toilet with the discarded, disposable article. However, where such packaging is composed of a water-resistant material, the aforementioned problems persist.

The use of lactic acid and lactide to manufacture a water-stable polymer is well known in the medical industry. Such polymers have been used in the past for making water-stable sutures, clamps, bone plates and biologically active controlled release devices. Processes developed for the manufacture of such polymers to be utilized in the medical industry have incorporated techniques which respond to the need for high purity and biocompatability in the final product. These processes, however, are typically designed to produce small volumes of high dollar-value products, with less emphasis on manufacturing cost and yield.

It is generally known that lactide polymers or poly (lactides) are unstable. However, the consequence of this instability has several aspects. One aspect is the biodegradation or other forms of degradation which occur when lactide polymers, or articles manufactured from lactide polymers, are discarded or composted after completing their useful life. Another aspect of such instability is the degradation of lactide polymers during processing at elevated temperatures as, for example, during melt-processing by end-user purchasers of polymer resins.

In the medical area there is a predominant need for polymers which are highly stable and therefore desirable for use in medical devices. Such a demand has historically been prevalent in the high value, low volume medical specialty market, but is now also equally prevalent in the low value, high volume medical market.

As described in U.S. Pat. No. 5,472,518, compositions comprised of multilayer polymer films are known in the art. The utility of such structures lies in the manipulation of physical properties in order to increase the stability or lifetime during use of such structure. For example U.S. Pat. No. 4,826,493 describes the use of a thin layer of hydroxybutyrate polymer as a component of a multilayer structure as a barrier film for diaper components and ostomy bags.

Another example of use of multilayer films is found in U.S. Pat. No. 4,620,999 which describes the use of a water soluble film coated with, or laminated to, a water insoluble film as a disposable bag. The patent describes a package for body waste which is stable to human waste during use, but which can be made to degrade in the toilet, at a rate suitable for entry into a sewage system without blockage, by adding a caustic substance to achieve a pH level of at least 12. Such structures are usually consist of a polyvinyl alcohol film layer coated with polyhydroxybutryate.

A similar excretion-treating bag allowing discarding in flush toilet or sludge vessel is disclosed in JP 61-42127. It is composed of an inner layer of water-resistant water-dispersible resin such as polylactide and an outer layer of polyvinyl alcohol. As disclosed in this patent, there are many examples of multilayer films that are utilized in disposable objects. Most of these examples consist of films or fibers which are comprised of external layers of an environmentally degradable polymer and an internal layer of water-responsive polymer. Typically, the external layers are comprised of polycaprolactone or ethylene vinyl acetate and the internal layer is comprised of polyvinyl alcohol. These examples, however, are all limited to compositions consisting of multilayers of different polymers, and do not encompass actual blends of different polymers.

A family of patents, EP 241178, JP 62-223112 and U.S. Pat. No. 4,933,182, describes a controlled release composition for treating periodontal disease. The controlled release compositions are comprised of a therapeutically effective agent in a carrier consisting of particles of a polymer of limited water solubility dispersed in a water soluble polymer. Although, the carrier of these inventions includes the use of more than one polymer, the disclosed carrier is not a blend because the water soluble polymer of limited solubility is incorporated in the water soluble polymer as particles ranging in average particle size from 1 to 500 microns.

The use of polymers for use in water-responsive articles is disclosed in U.S. Pat. Nos. 5,508,101, 5,567,510, and 5,472,518. This group of patents discloses a series of water-responsive compositions comprising a hydrolytically degradable polymer and a water soluble polymer. The compositions of this group, however, consist of articles constructed from polymers which are first formed into fibers or films and then combined. As such, the compositions are actually mini-layers of the individual polymer films or fibers. Therefore, although the fibers and films of the polymers of such compositions are considered to be in very close proximity with one another, they are not actual blends. The dispersion of one polymer within another in these compositions, is not viewed as approximately uniform since the individual polymers are essentially distinct and separate fibers or films.

U.S. Pat. No. 5,525,671 to Ebato et al. discloses a method of making a linear lactide copolymer from a lactide monomer and a hydroxyl group containing monomer. The polymer disclosed by Ebato is a linear lactide copolymer that is formed by reacting two monomers to form a linear polymer with a block or random structure. Ebato does not disclose graft copolymers.

Polymer blend compositions for making fibers and films that are optimally combined are desirable because they are highly stable. Optimal combination of polymers means that the polymers are connected as closely as possible without the requirement of co-polymerization. Although blended polymer compositions are known, improved polymer blends wherein the fibers and films are more intimately connected are desirable since the resulting composition is then more stable, pliable and versatile.

In addition to the need for polymer compositions that are highly stable, and therefore, suitable for regular use in most disposable articles, there is a simultaneous need for such polymer compositions to be water-responsive. What is needed therefore, is a material that may be utilized for the manufacture of disposable articles and which is water-responsive. Such material should be versatile and inexpensive to produce. The material should be stable enough for intended use but subject to degradation under predetermined conditions.

Moreover, there is an increased emphasis on environmentally safe materials and coatings. These coatings reduce the use of solvent-based coatings and rely, to an ever increasing degree, on polar coatings, such as water-based material. The utility of the graft copolymers of this invention includes, but would not be limited to, materials have a greater affinity for a polar coating.

Therefore, it is an object of this invention to make biodegradable polymer compositions, films, fibers and articles.

Another object of this invention is to make thermally processable polymer compositions, films, fibers and articles.

Another object of this invention to make commercially viable polymer compositions, films, fibers and articles.

Another object of this invention to make thermally processable, biodegradable polymer compositions, films, fibers and articles which are more compatible with polar polymers and other polar substrates.

Another object of this invention is to make water-responsive, biodegradable polymer compositions, films, fibers and articles.

Another object of this invention is to make water-responsive, biodegradable polymer compositions, films, fibers and articles with improved mechanical and physical properties.

Another object is to develop a method of making water-responsive compositions, films, fibers and articles which may be tailored to be water-dispersible, water-weakenable or water-stable.

SUMMARY OF THE INVENTION

This invention discloses water-responsive compositions, films, fibers and articles comprising a blend of polyvinyl alcohol and a polylactide. The water-responsive compositions, films, fibers and articles described herein can have a wide range of responsiveness ranging form water-dispersible, to water-degradable and to water-stable. The present invention also discloses a method of controlling the water-responsiveness of the compositions and films fibers and articles comprising the compositions by varying the amount of polyvinyl alcohol from about 1 to about 99 weight percent of the blend and varying the amount of polylactide from about 1 to about 99 weight percent of the blend. The composition ranges responsible for each type of water responsiveness are disclosed.

Films made from compositions of the present invention are useful as components of flushable personal care products, such as baffle films for feminine and adult care products and outer covers for diapers, etc. The water-responsive blends and films and fibers disclosed in this invention have the unique advantage of being biodegradable so that the blends, films, fibers and articles made from the blends and films can be degraded in aeration tanks, by aerobic degradation, and anaerobic digesters, by anaerobic degradation, in waste water treatment plants. Therefore, articles comprising the blends of this invention will not significantly increase the volume of sludge accumulated at waste water treatment plants.

BRIEF DESCRIPTION OF THE FIGURES

The invention will be more fully understood and further advantages will become apparent when reference is made to the following detailed description of the invention and the drawings in which.

DETAILED DESCRIPTION OF THE INVENTION

Polylactide (abbreviated herein as PLA) resins are produced by different synthetic methods, such as ring-opening polymerization of lactide or direct condensation polymerization from lactic acid. Both methods of polymerization are useful for this invention. PLA is a biodegradable polymer and has the chemical structure:

$[-CH(CH_3)CO_2-]_n$.

The PLA component in the blends and compositions described in the following Examples were made by using a reagent grade PLA purchased from Aldrich Chemical Company of Milwaukee, Wis. (Aldrich Catalog number 42,232-6). The PLA purchased from Aldrich Chemical Company is biodegradable and has number-average molecular weight of approximately 60,000 and a weight-average molecular weight of approximately 144,000. This PLA is made up primarily of the L-isomer and has a glass transition temperature ($T_g$) of 60° C. Any PLA can be selected for use in this invention, and the molecular weights of the PLA may vary depending on the desired properties and use. The PLA component can optionally be modified or grafted prior to or contemporaneously with the blending of the PLA with poly(vinyl alcohol).

Ethylenically unsaturated monomers containing a polar functional group, such as hydroxyl, carboxyl, amino, carbonyl, halo, thiol, sulfonic, sulfonate, etc. are desirable for modifying the PLA of this invention. Suggested ethylenically unsaturated polar monomers include, but are not limited to, 2-hydroxyethyl methacrylate (hereinafter HEMA), poly(ethylene glycol) methacrylates (hereinafter PEG-MA) including poly(ethylene glycol) ethyl ether methacrylate, poly(ethylene glycol) acrylates, poly(ethylene glycol) ethyl ether acrylate, poly(ethylene glycol) methacrylates with terminal hydroxyl groups, acrylic acid, maleic anhydride, itaconic acid, sodium acrylate, 3-hydroxypropyl methacrylate, acrylamide, glycidyl methacrylate, 2-bromoethyl acrylate, carboxyethyl acrylate, methacrylic acid, 2chloroacrylonitrile,. 4-chlorophenyl acrylate, 2-cyanoethyl acrylate, glycidyl acrylate, 4-nitrophenyl acrylate, pentabromophenyl acrylate, poly(propylene glycol) methacrylate, poly(propylene glycol) acrylate, 2-propene-1-sulfonic acid and its sodium salt, sulfo ethyl methacrylate, 3-sulfopropyl methacrylate, and 3-sulfopropyl acrylate. A particularly desired poly(ethylene glycol) methacrylate is poly(ethylene glycol) ethyl ether methacrylate. Preferred ethylenically unsaturated monomers containing a polar functional group are referred to herein as polar vinyl monomers and include, but are not limited to, 2-hydroxyethyl methacrylate (abbreviated herein as HEMA) and poly(ethylene glycol) methacrylate (abbreviated herein as PEG-MA).

It is expected that a wide range of polar vinyl monomers would be capable of imparting the same effects as HEMA and PEG-MA to polylactide resins and would be effective monomers for grafting. The grafted PLA may contain from 1 to 20 percent by weight of grafted polar monomer, oligomer, polymer or a combination thereof. Preferably, the grafted PLA contains 2.5 to 20 percent by weight of grafted polar monomers, oligomers, or polymers, and most preferably 2.5 to 10 by weight of grafted polar monomers, oligomers, or polymers, Both the HEMA (Aldrich Catalog number 12,863-8) and the PEG-MA (Aldrich Catalog number 40,954-5) used in the Examples were supplied by Aldrich Chemical Company. Specifically, the PEG-MA purchased from Aldrich Chemical Company was poly(ethylene glycol) ethyl ether methacrylate having a number average molecular weight of approximately 246 grams per mol.

The method for making modified PLA compositions has been demonstrated by a reactive-extrusion process that grafts a monomer or a mixture of monomers onto the PLA. The grafting reaction can also be performed in other reaction devices as long as the necessary mixing of PLA and the monomer, oligomer, polymer or a mixture thereof is achieved and enough energy is provided to effect the grafting reaction between the PLA and the monomer, oligomer, polymer or a mixture thereof.

Other reactive ingredients which may be added to the compositions of this invention include initiators such as Lupersol 101, a liquid, organic peroxide available from Elf Atochem North America, Inc. of Philadelphia, Pa. Free radical initiators useful in the practice of this invention include acyl peroxides such as benzoyl peroxide; dialkyl; diaryl; or aralkyl peroxides such as di-t-butyl peroxide; dicumyl peroxide; cumyl butyl peroxide; 1,1 di-t-butyl peroxy-3,5,5-trimethylcyclohexane; 2,5-dimethyl-2,5-di(t-butylperoxy) hexane; 2,5-dimethyl-2,5-bis (t-butylperoxy) hexyne-3 and bis(a-t-butyl peroxyisopropylbenzene); peroxyesters such as t-butyl peroxypivalate; t-butyl peroctoate; t-butyl perbenzoate; 2,5-dimethylhexyl-2,5-di(perbenzoate) t-butyl di(perphthalate); dialkyl peroxymonocarbonates and peroxydicarbonates; hydroperoxides such as t-butyl hydroperoxide, p-methane hydroperoxide, pinane hydroperoxide and cumene hydroperoxide and ketone peroxides such cyclohexanone peroxide and methyl ethyl ketone peroxide. Azo compounds such as azobisisobutyronitrile may also be used.

Furthermore, other components known in the art may be added to the graft polymers of this invention to further enhance the properties of the final material. For example, polyethylene glycol may be further added to improve melt viscosity. Additives of other types may also be incorporated to provide specific properties as desired. For example, anti-static agents, pigments, colorants and the like may be incorporated in to the polymer composition. Additionally, processing characteristics may be improved by incorporating lubricants or slip agents into blends made from polymers of the invention. All of these additives are generally used in relatively small amounts, usually less than 3 weight percent of the final composition.

The mixture of the polylactide and the polar monomer, oligomer, or polymer is subjected to mechanical deformation in a suitable mixing device, such as a Bradender Plasticorder, a roll mill, a single or multiple screw extruder, or any other mechanical mixing device which can be used to mix, compound, process or fabricate polymers. A particularly desirable reaction device is an extruder having one or more ports. In a preferred embodiment, the reaction device is a co-rotating, twin-screw extruder, such as a ZSK-30 twin-screw compounding extruder manufactured by Werner & Pfleiderer Corporation of Ramsey, N.J. This extruder allows multiple feeding and venting ports.

The presence of PLA or modified PLA in blends with poly(vinyl alcohol) (abbreviated herein as PVOH) reduces the water sensitivity of the PVOH in use. Because PLA is a biodegradable polymer, the presence of PLA in blends with PVOH increases the biodegradability of the finished film, fibers, and other articles comprising the blend. PLA grafted with a polar monomer or a mixture of monomers is preferred for enhanced compatibility with PVOH in order to obtain superior processing and mechanical and physical properties and to make improved films, fibers and articles comprising blends of PLA and PVOH. The amount of PLA relative to the amount of PVOH in the blends can be varied to vary the water responsiveness of the blends and composition, films, fibers and articles comprising such blends. Specifically, the amount of water-soluble PVOH in the blends can be increased to increase the water responsiveness of the blends.

Desirably, the PVOH component of the compositions of the present invention is a thermoplastic. Suggested thermoplastic PVOH resins are available from Nippon Gohsei, Japan. A particularly suggested thermoplastic PVOH resin is sold under the trade name Ecomaty AX10000 PVOH and is a cold-water soluble polymer synthesized from partially hydrolyzed polyvinyl acetate containing side branches. Other PVOH resins that are thermoplastic can also be used as the PVOH component of the compositions of the present invention and PVOH may contain nonpolar side chains. Examples of other applicable PVOH are disclosed in U.S. Pat. No. 6,020,425 entitled "Unmodified Polyvinyl Alcohol Films and Fibers and Methods of Making the Same," issued on Feb. 1, 2000, this patent is incorporated in its entirety.

As used herein, the term "water-dispersible" means that the composition dissolves or breaks into pieces smaller than a 20 mesh after being immersed in water for approximately five minutes. The term "water-disintegratable" means that the composition breaks into multiple pieces within five minutes of immersion in water and that some of the pieces will be caught by a 20 mesh screen without slipping through in the same manner as a thread through the eye of a needle.

The term "water-weakenable" means that the composition remains in one piece but weakens and loses rigidity after five minutes of immersion in water and becomes drapeable, i.e. it bends without an external force applied thereto when it is held by one side at a horizontal position. The term "water-stable" means that the composition does not become drapeable after five minutes of immersion in water and remains in one piece after the water response test.

As used herein, the term "graft copolymer" means a copolymer produced by the combination of two or more chains of constitutionally or configurationally different features, one of which serves as a backbone main chain, and at least one of which is bonded at some point(s) alone the backbone and constitutes a side chain. The molar amount of grafted monomer, oligomer or polymer, i.e. side-chain species, may vary but should be greater than molar amount of the parent species. The term "grafted" means a copolymer has been created which comprises side chains or species bonded at some point(s) along the backbone of a parent polymer. The term "blend" as applied to polymers means an intimate combination of two or more polymer chains of constitutionally or configurationally different features which are not bonded to each other. Such blends may be homogenous or heterogeneous. (See Sperling, L. H., *Introduction to Physical Polymer Science* 1986 pp. 44–47 which is herein incorporated by reference in its entirety.) Preferably, the blend is created by combining two or more polymers at a temperature above the melting point of each polymer.

The present invention is illustrated in greater detail by the following specific Examples. It is to be understood that these Examples are illustrative embodiments and that this invention is not to be limited by any of the Examples or details in the description. Rather, the claims appended hereto are to be construed broadly within the scope and spirit of the invention.

EXAMPLES

Example 1

A co-rotating, twin-screw extruder, ZSK-30 manufactured by Werner & Pfleiderer Corporation of Ramsey, N.J., was used to manufacture the modified PLA of the Examples. The diameter of the extruder was 30 mm. The length of the screws was 1388 mm. This extruder had 14 barrels, numbered consecutively 1 to 14 from the feed hopper to the die. The first barrel, barrel #1, received the PLA and was not heated but cooled by water. The vinyl monomer, HEMA, was injected into barrel #5 and the Lupersol 101 peroxide by Atochem was injected into barrel #6. Both the monomer and the peroxide were injected via a pressurized nozzle injector. A vacuum port for devolatilization was included at barrel #11. The die used to extrude the modified PLA strands had four openings of 3 mm in diameter which were separated by 7 mm. The modified PLA strands were then cooled in a cold water bath and then pelletized.

The PLA was fed into the extruder with a volumetric feeder at a throughput of 20 lb/hr. The HEMA and the peroxide were injected into the extruder at throughputs of 1.8 lb/hr and 0.09 lb/hr, respectively. The screw speed was 300 rpm.

The following extruder barrel set temperatures were used during the extrusion run:

| Zone 1 | Zone 2 | Zone 3 | Zone 4 | Zone 5 | Zone 6 | Zone 7 |
|---|---|---|---|---|---|---|
| 180° C. | 180° C. | 180° C. | 180° C. | 180° C. | 170° C. | 160° C. |

The vacuum was turned on for devolatization at barrel #11 and the process was allowed to stabilize. The extruded HEMA grafted PLA (PLA-g-HEMA) strands were cooled in a cold water bath and then pelletized.

Melt rheology tests were performed on the modified and unmodified PLA on a Goettfert Rhoegraph 2000 available from Goettfert in Rock Hill, S.C. The modified PLA of this Example was prepared with 9 weight percent HEMA and 0.45 weight percent Lupersol. The weight percentages of the HEMA and Lupersol were based on the weight of the PLA.

The melt rheology tests were performed at 180° C. with a 30/1 (length/diameter) mm die. The apparent melt viscosity was determined at apparent shear rates of 50, 100, 200, 500, 1000, and 2000 1/s. A rheology curve was plotted for each material of the apparent viscosity versus the apparent shear rates below.

| Sample Comment App. Shear Rate (l/s) | PLA, Aldrich Extruded Control App. Shear Visc. (Pa s) | PLA-g-HEMA (9%, 0.45%) Grafted PLA App. Shear Visc. (Pa s) |
|---|---|---|
| 49.997 | 325.7 | 97.71 |
| 99.994 | 252.42 | 97.71 |
| 199.99 | 207.63 | 65.14 |
| 499.97 | 154.71 | 55.369 |
| 1000 | 112.35 | 46.407 |
| 2000 | 82.235 | 38.675 |

Figure 1:
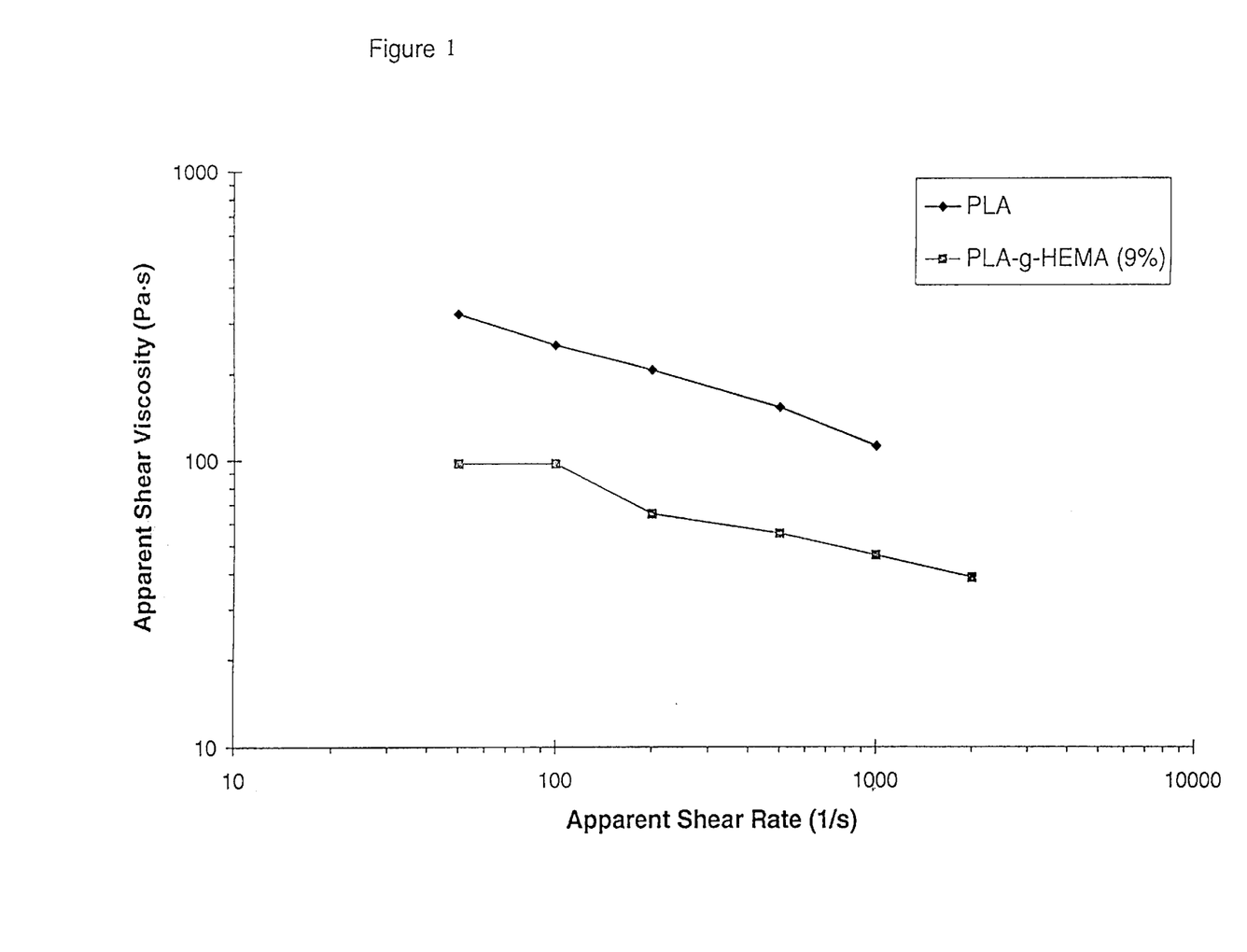
FIG. 1 is a plot of the viscosity versus the shear rate of a grafted polylactide in accordance with the present invention and an ungrafted polylactide, demonstrating the decrease in viscosity of grafted polylactide versus ungrafted polylactide.

The apparent melt viscosities at the various apparent shear rates were plotted and rheology curves for the unmodified PLA and the modified PLA of the above Example were generated as shown in FIG. 1. The rheology curve of the modified PLA demonstrates the reduced viscosities of the modified PLA when compared to the unmodified PLA. These reduced viscosities of the modified PLA result in improved processability of the modified PLA. The grafting of polar monomers, oligomers or polymers onto PLA also results in improved compatibility with both polar materials and polar substrates.

Example 2

Films Made from Blends Comprising PVOH and Modified PLA or Unmodified PLA

The water-responsive films of the following Examples are composed of melt blends of unmodified or modified PLA and PVOH. The range of the compositions for water-responsive films vary from about 1 to about 99 weight percent of unmodified or modified PLA in the blend. The presence of PLA or modified PLA in the blend used to make films reduces the water sensitivity of pure PVOH in use. PLA grafted with a polar monomer or a mixture of monomers is preferred for enhanced compatibility with PVOH in order to obtain superior mechanical and physical properties. The modified PLA used in the blends is as described above in Example 1 and the unmodified PLA used in the blends was that as supplied by Aldrich Chemical Company. The PVOH used in the blends was Ecomaty AX10000 supplied by Nippon Gohsei, Japan. Ecomaty AX10000 PVOH resin is a cold-water soluble polymer synthesized from partially hydrolyzed polyvinyl acetate containing side branches.

Extrusion Process for Polymer Blending

Water-responsive blend compositions were prepared by a melt extrusion process. It is preferred to blend or mix the two components in an extruder such as a twin-screw or even a single screw extruder under appropriate temperature and shear/pressure conditions. The blending process can also be performed in a batchwise mixing device, such as a melt mixer or a kneader, which is discussed in the next section. Both PVOH and modified PLA can be fed to an extruder either simultaneously or in sequence to minimize any adverse effects on the polymers such as degradation or discoloration.

In these Examples, the extrusion process of the blends was performed using a Haake TW-100 counter-rotating, twin screw extruder. The extrusion set temperatures for the four heating zones were 170, 180, 180 and 168° C., respectively. The screw speed was 150 rpm. A resin mixture of PLA or modified PLA and PVOH was fed into the extruder at a rate of 10 lb/hr. The melt was extruded, air-cooled and then pelletized.

Extruded blend compositions which contained 20, 30, and 40 weight percent of either unmodified PLA or modified PLA and 80, 70 and 60 weight percent PVOH, respectively, were produced and used to make films in this Example.

Melt Mixing Process for Polymer Blending

Water-responsive blend compositions were also prepared by a melt mixing process. In these Examples, the melt mixing process was performed using a Haake Rheomix® 600, a counter-rotating, twin roller mixer. The mixer set temperature was 180° C. The screw speed was 150 rpm. 70 grams of total resin mixture was fed into the mixer and blended for five minutes. The melt was removed from the mixer and then cooled in air.

Melt mixer compositions containing 30, 40, 50 and 60 weight percent HEMA grafted PLA and 70, 60, 50 and 40 weight percent PVOH, respectively, were produced and used to make the films in this Example.

Film Preparation

A film was prepared for each blend composition using a Carver hot press with two heated platens at a temperature of 190° C. and a pressure of 15,000 psi for about one minute. The thickness of the films in this Example were approximately 4 mils. The thickness of the films can be either increased or decreased depending on the final use and properties desired.

Water Response Test of the HEMA grafted PLA/PVOH Films

For each of the compositions, a section of the prepared film was cut measuring about ¼ of an inch by about ½ of an inch. The water-response test involved using a pair of tweezers to hold the section of the film, immersing it into a scintillation vial filled with 20 milliliters of water and holding it there for five minutes. After five minutes, a cap was placed on the scintillation vial and the vial was placed in a Model 75 Shaker (available from Burrell Corp., Pittsburgh, Pa.). The vial was shaken for 30 seconds with the shaker set at maximum speed. If the film began to disperse or disintegrate, the contents of the scintillation vial were emptied through a 20 mesh screen (20 mesh U.S.A. Standard Testing Sieve, ASTM E- 11 Specification, No. 20). The vial was then rinsed with 20 milliliters of water from a squeeze bottle to remove any remaining film pieces and emptied through the sieve. If the film did not disperse or disintegrate, the film was observed for any loss in rigidity.

Water Response Map for Extruder and Mixer Blended Films and Compositions

Films made from blend compositions were water dispersible up to about 40 weight percent of modified or unmodified PLA in the blend. The films made from blends with about 60 or greater weight percent of unmodified or modified PLA were water stable. The films made from blends between these two ranges should be considered water weakenable. The films made from blends with about 50 weight percent of modified or unmodified PLA were water weakenable.

Disposable Articles Comprising PLA and PVOH

Water-responsive and water-stable blends of PLA and PVOH and compositions comprising such blends and films and fibers comprising such blends have utility in the manufacture of disposable articles, particularly disposable personal care articles. It would be desirable to construct personal care articles, such as diapers, sanitary napkins, adult incontinence garments, bandages, surgical masks, gowns and foot covers and the like so that the article can be easily and safely disposed by flushing the article down a conventional toilet. Specifically, it would be highly desirable to manufacture diapers, feminine pads, pantiliners sanitary napkins and even training pants that can be flushed down a conventional toilet without fear of clogging the toilet or any components of the sewage system beyond the toilet. Articles that can be disposed of by flushing would decrease the current demand for land fill space and decrease incineration costs. Articles made from such compositions have biodegradability and can reduce the amount of sludge produced in wastewater treatment plants. The biodegradablilty of the compositions is also beneficial if used or soiled personal care products comprising the compositions are accidentally discarded in municipal waste and subsequently disposed at landfill.

While the following description is made in the context of a disposable diaper and a disposable feminine pad, it is readily apparent that compositions of the present invention and films and fibers comprising compositions of the present invention can also be employed in various other types of articles, such as sanitary napkins, pantiliners, incontinence garments, bandages, absorbent wipes, training pants and the like. All of these articles are contemplated as being within the scope of the present invention.

Figure 2:
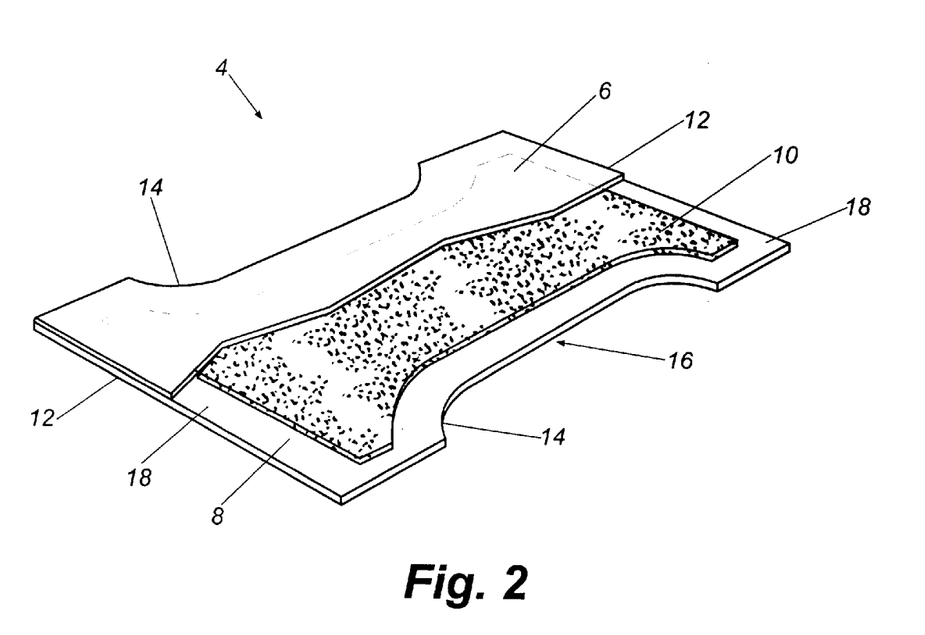
FIG. 2 representatively shows a perspective view of a disposable garment, such as a diaper or a adult incontinence garment.

Referring to FIG. 2, disposable diaper 4 includes a liquid-permeable inner liner 6, a liquid-impermeable outer layer, such as backsheet 8, and an absorbent core layer, such as batt 10, with the batt located between the liner 6 and the backsheet 8. The inner liner 6 and the backsheet 8 are larger than the absorbent batt 10, and have end marginal portions 12 extending beyond the ends of batt 10. The liner 6 and backsheet 8 also have side marginal portions 14 extending beyond the sides of the batt 10. Typically, liner 6 and backsheet 8 are secured to each other along the marginal portions 12 and 14. Liner 6 may be any soft, flexible porous sheet which passes fluids therethrough, and may, for example, be comprised of a nonwoven web or sheet of polyolefin fibers, such as polypropylene fibers, polylactide fibers, fibers comprising one of the compositions of the present invention or a mixture comprising such fibers. In one embodiment, the fibers can be bound with a water-sensitive or ion triggerable binder. A desirable ion triggerable binder is water soluble or water dispersible at ion concentrations below the typical ion concentration of urine but is water stable at concentrations above the typical ion concentration of urine. Desirable ion-triggerable binder and adhesive compositions are disclosed in U.S. Pat. No. 5,986,004 which is hereby incorporated herein in its entirety. The liner 6 may be comprised of wet strength tissue paper, a spunwoven filament sheet, or the like. In addition, the liner 6 may be treated with a surfactant to aid in liquid transfer.

Backsheet 8 is a liquid-impermeable layer, and may be comprised of a thin web or sheet of plastic film of one or more of the compositions of the present invention. For example, backsheet 8 can be formed from a mutilayer film comprising a first layer of water-soluble, water-dispersible or water-dispersible composition of the present invention and at least one second layer of a water-stable material such a polyolefin, a polyester or one of the water-stable compositions disclosed herein. The backsheet can be coextruded from a water-soluble, water dispersible or water-disintegratable composition and a water-stable composition. The backsheet 8 is adhered to the liner 6 with a water-stable layer of the multilayer film comprising the backsheet facing the liner and the interior of the diaper so that urine does not adversely affect the backsheet. The thickness of the water-stable layer should be selected such that when the backsheet is exposed to water the water-soluble, water-dispersible or water-disintegratable portion of the backsheet dissolves, disperses or disintegrates, respectively, and the water-stable portion of the backsheet disintegrates. The backsheet may be transparent or may have an embossed or matt surface to render it opaque.

Absorbent batt 10 may be of any suitable material, and is generally a blend of cellulosic material and superabsorbent material. An example of cellulosic material useful as a component of batt 10 includes an airformed batt of wood pulp fibers commonly known as "fluff". The superabsorbent material may be particulate superabsorbent or a fibrous superabsorbent. One example of a particulate superabsorbent includes, but is not limited to, a partially neutralized, crosslinked poly(acrylic acid). However, the fibers can be staple fibers of any superabsorbent polymer. Commercial examples of superabsorbent materials include OASIS® staple superabsorbent fibers (partially neutralized polyacrylic acid, available from Technical Absorbents of the United Kingdom) and FIBERDRI® staple superabsorbent fibers (hydrolyzed salt of isobutylene-co-maleic anhydride, available from Camelot Superabsorbent Ltd. of Calgary, Canada).

Absorbent, creped wadding or tissue sheets can be located between absorbent batt 10 and liner 6 and backsheet 8, respectively. Liner 6, backsheet 8, and absorbent batt 10 may be combined with one another in any suitable manner to form a finished diaper. The elements may be bonded to one another by strips or patterns of hot melt or pressure sensitive adhesive, overall or patterned heat sealing, strips of double faced, pressure sensitive adhesive tape, or the like. Alternatively, the elements can be bonded by an ultrasonic method of bonding. A particularly effective bonding system employs spaced, parallel lines of hot melt adhesive placed on the interior surface of backsheet 8. The absorbent batt is bonded to the backsheet along portions of the adhesive lines, and liner 6 is bonded to backsheet 8 along other portions of the adhesive lines that are located within the marginal portions 12 and 14 but outside the region of batt 10. In a desirable embodiment, the adhesive is also water responsive or water sensitive and disintegrates, disperses or dissolves on contact with water.

Diaper 4 has a generally hourglass or I-shape, which includes a narrowed crotch section 16 near the center of the diaper and includes waistband sections 18 at each end of the diaper. Elongate elastic means can be secured in place adjacent absorbent batt 10 and on each side thereof to develop gathered elastic leg portions that are conformable with an infant's legs. Conventional pressure sensitive tapes or VELCRO hook-and-loop fasteners (not shown) can also be attached to one waistband section 18. Diaper 4 is fitted to an infant with inner liner 6 against the infant's skin. One waistband portion encircles part of the infant's waist and the other waistband portion encircles the balance of the infant's waist. The two waistband portions are overlapped and joined together by pressure sensitive adhesive tapes or velcro fastener which operate to hold the diaper in place.

Figure 3:
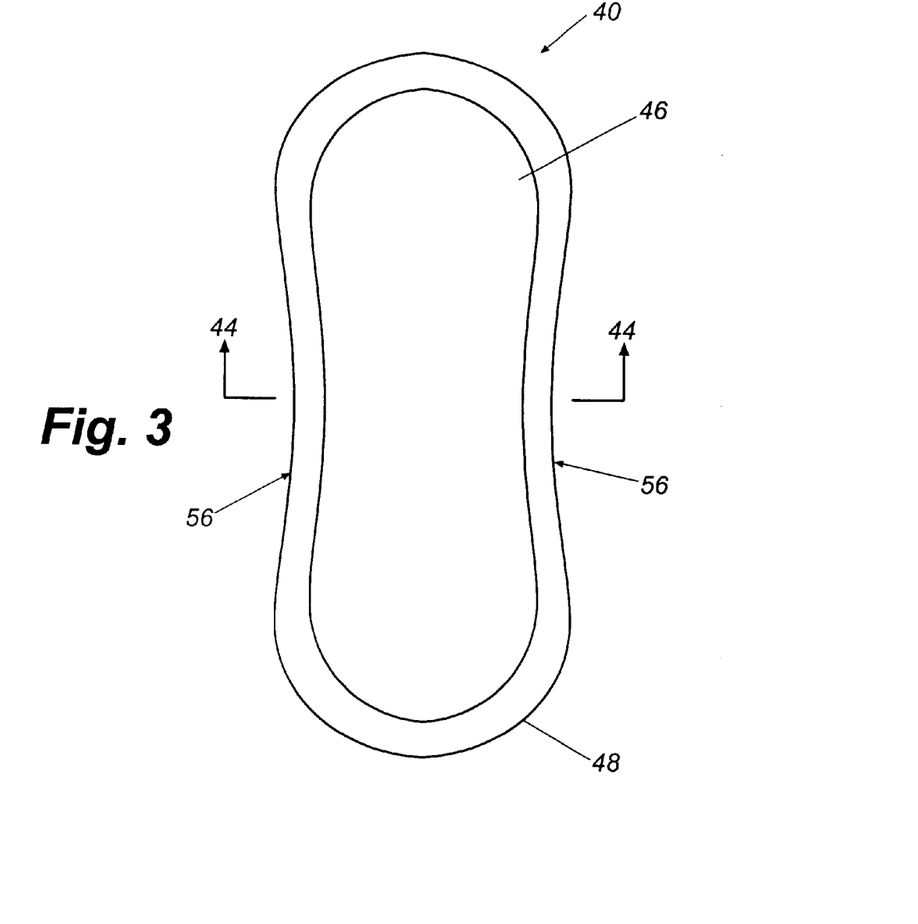
FIG. 3 representatively shows a top view of a feminine care article, such as a feminine pad.
Figure 4:
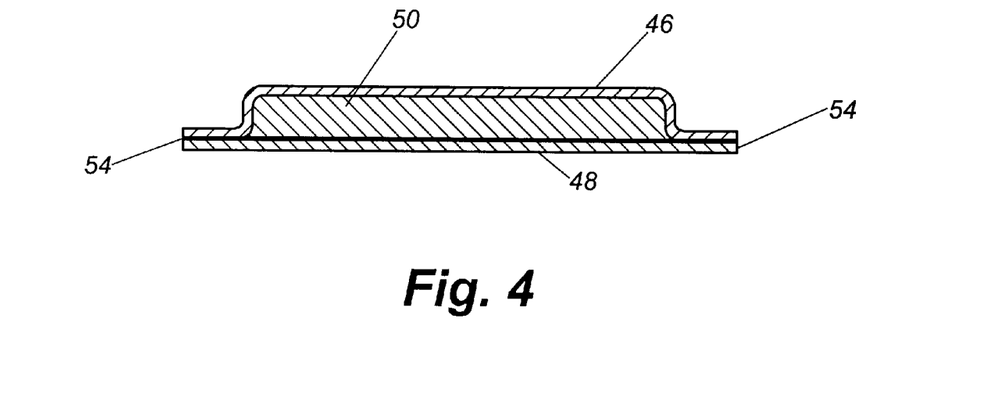
FIG. 4 is a cross-sectional, elevational side view of the feminine care article taken along section 44–44 of FIG. 3.

Referring to FIG. 3 and FIG. 4, an exemplary feminine pad or feminine napkin 40 includes a liquid-permeable top sheet 46, a liquid-impermeable outer layer, such as backsheet 48, and an absorbent layer, such as batt 50, with the batt located between the top sheet 46 and the backsheet 48. FIG. 4, is a cross-sectional, elevational side view of the feminine pad 40 taken along section 44—44 of FIG. 3. The top sheet 46 and the backsheet 48 are larger than the absorbent batt 50, and have side and end marginal portions 54 extending beyond the ends of batt 50. Typically, top sheet 46 and backsheet 48 comprise a narrowed crotch section 56 and are secured to each other along the marginal portions 54. Top sheet 46 may be any soft, flexible porous sheet which passes fluids therethrough, and may, for example, be comprised of a nonwoven web or sheet of polyolefin fibers, such as polypropylene fibers, polylactide fibers, fibers comprising one of the compositions of the present invention or a mixture of fibers. The fibers of the top sheet can be bound with a water-sensitive or ion triggerable binder so that the top sheet will disntegrate and disperse on contact with water.

Backsheet 48 is a liquid-impermeable layer, and may be comprised of a thin web or sheet of plastic film of one or more of the compositions of the present invention. For example, backsheet 48 can be formed from a mutilayer film comprising a first layer of water-soluble, water-dispersible or water-disintegratable composition of the present invention and at least one second layer of a water-stable material such a polyolefin, a polyester or one of the water-stable compositions disclosed herein. The backsheet can be coextruded from a water-soluble, water dispersible or water-disintegratable composition and a water-stable composition. The backsheet 48 is adhered to top sheet 46 with a water-stable layer of the multilayer film comprising the backsheet facing the top sheet and the interior of the feminine so that menses and/or urine do not adversely affect the backsheet. The thickness of the water-stable layer should be selected such that when the backsheet is exposed to water the water-soluble, water-dispersible or water-disintegratable portion of the backsheet dissolves, disperses or disintegrates, respectively, and the water-stable portion of the backsheet disintegrates.

Absorbent batt 50 may be of any suitable material, and is generally a cellulosic material, such as an airformed batt of wood pulp fibers commonly known as "fluff". A superabsorbent material can be included in the absorbent layer. Top sheet 46, backsheet 48, and absorbent batt 50 may be combined with one another in any suitable manner to form a finished feminine pad. The elements may be bonded to one another by strips or patterns of hot melt or pressure sensitive adhesive, overall or patterned heat sealing, or the like. For example, the elements of the can be bonded by an ultrasonic method instead of with an adhesive composition. A particularly effective bonding system employs spaced, parallel lines of hot melt adhesive placed on the interior surface of backsheet 48. The absorbent batt is bonded to the backsheet along portions of the adhesive lines, and liner 46 is bonded to backsheet 48 along other portions of the adhesive lines that are located within the marginal portions but outside the region of batt 50. In a desirable embodiment, the adhesive is also water responsive or water sensitive and disintegrates, disperses or dissolves on contact with water.

It is to be understood that these Examples are illustrative embodiments and that this invention is not to be limited by any of the Examples or details in the description. Rather, the claims appended hereto are to be construed broadly within the scope and spirit of the invention.

We claim:

1. A personal care article comprising a film or a nonwoven fabric, said film nonwoven fabric comprising a melt blend of poly(vinyl alcohol) and a polylactide, wherein said polylactide is grafted with a polar monomer, oligomer, polymer or a combination thereof.

2. The personal care article of claim 1, wherein said polylactide is modified.

3. The personal care article of claim 2, wherein said polylactide is grafted with a polar monomer, oligomer, or polymer or a combination thereof.

4. The personal care article of claim 3, wherein said the polar monomer, oligomer, or polymer is selcted from the group consisting of 2-hydroxyethyl methacrylate, poly(ethylene glycol) methacrylates, poly(ethylene glycol) ethyl ether methacrylate, poly(ethylene glycol) acrylates, poly(ethylene glycol) ethyl ether acrylate, poly(ethylene glycol) methacrylates with terminal hydroxyl groups, acrylic acid, maleic anhydride, itaconic acid, sodium acrylate, 3-hydroxypropyl methacrylate, acrylamide, glycidyl methacrylate, 2-bromoethyl acrylate, carboxyethyl acrylate, methacrylic acid, 2-chloroacrylonitrile, 4-chlorophenyl acrylate, 2-cyanoethyl acrylate, glycidyl acrylate, 4-nitrophenyl acrylate, pentabromophenyl acrylate, poly(propylene glycol) methacrylate, poly(propylene glycol) acrylate, 2-propene-1-sulfonic acid and its sodium salt, sulfo ethyl methacrylate, 3-sulfopropyl methacrylate, and 3-sulfopropyl acrylate.

5. The personal care article of claim 1, wherein said polylactide is graft copolymer of a polylactide and from about 1 weight percent to about 30 weight percent of a polar monomer, oligomer, or polymer or a combination thereof relative to the weight of the polylactide.

6. The personal care article of claim 3, wherein said polar monomer is an ethylenically unsaturated monomer containing at least one polar functional group or said oligomer or said polymer is an oligomer or a polymer polymerized from an ethylenically unsaturated monomer containing at least one polar functional group.

7. The personal care article of claim 6, wherein said at least one polar functional group is a hydroxyl, carboxyl or sulfonate group or a combination thereof.

8. The personal care article of claim 6, wherein said at least one polar functional group is a hydroxyl group.

9. The personal care article of claim 5, wherein said polar monomer is a polar vinyl monomer.

10. The personal care article of claim 3, wherein said polar monomer, oligomer, or polymer is selected from the group consisting of 2-hydroxyethyl methacrylate and polyethylene glycol methacrylate and derivatives thereof.

11. The personal care article of claim 3, wherein said polar monomer, oligomer, or polymer is selected from the group consisting of 2-hydroxyethyl methacrylate and its derivatives.

12. The personal care article of claim 1, wherein said blend comprises about 1 to about 99 weight percent poly(vinyl alcohol) and about 99 to about 1 weight percent polylactide.

13. The personal care article of claim 12, wherein said blend comprises about 1 to about 40 weight percent polylactide and is water-dispersible.

14. The personal care article of claim 1, wherein said personal care article is selected from the group consisting of diapers, incontinence products, training pants, feminine pads and pantiliners.

15. A personal care article comprising a melt blend of a poly(vinyl alcohol) and a modified polylactide comprising a polylactide backbone with a plurality of polar monomers, oligomers, polymers or a combination thereof grafted onto said polylactide backbone.

16. A method of varying the water responsiveness of a composition comprising the steps of:

a) selecting a specific amount of a poly(vinyl alcohol) and a specific amount of a graft modified polylactide, wherein said polylactide is grafted with a polar monomer, oligomer, polymer or a combination thereof;

b) melt blending the specific amount of poly(vinyl alcohol) with the specific amount of graft modified polylactide; and c) forming a personal care article or a component of the personal care article from the melt blend.

17. The method of claim 16, wherein said polylactide is modified prior to blending with the poly(vinyl alcohol).

18. The method of claim 17, wherein said polylactide is modified by the steps comprising:

a) combining a polylactide and a polar monomer, oligomer, or polymer in a reaction vessel; and b) providing sufficient energy to the combination of said polylactide and said polar monomer, oligomer, or polymer in order to modify said polylactide composition.

19. The method of claim 16, wherein the film is water-dispersible and comprises about 1 to about 40 weight percent polylactide and about 60 to about 99 weight percent poly(vinyl alcohol).

20. The method of claim 16, wherein the film is water-weakenable and comprises about 40 to about 60 weight percent polylactide and about 40 to about 60 weight percent poly(vinyl alcohol).

21. The method of claim 16, wherein the film is water-stable and comprises about 60 to about 99 weight percent polylactide and about 1 to about 40 weight percent poly(vinyl alcohol).

22. The method of claim 16, wherein the blending is performed by melt extrusion.

* * * * *